United States Patent
Amoah

(10) Patent No.: US 7,131,445 B2
(45) Date of Patent: Nov. 7, 2006

(54) ELECTROSURGICAL METHOD AND APPARATUS

(75) Inventor: Francis Amoah, Cardiff (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 10/727,618

(22) Filed: Dec. 5, 2003

(65) Prior Publication Data

US 2004/0122420 A1    Jun. 24, 2004

Related U.S. Application Data

(60) Provisional application No. 60/445,455, filed on Feb. 7, 2003.

(30) Foreign Application Priority Data

Dec. 23, 2002    (GB) ................................ 0230055.6

(51) Int. Cl.
*A61B 19/00*    (2006.01)

(52) U.S. Cl. .................... 128/898; 606/31; 606/42; 606/102

(58) Field of Classification Search ........ 607/100–102; 606/27–37, 38–42, 45–52
See application file for complete search history.

(56) References Cited

U.S. PATENT DOCUMENTS

| | | | |
|---|---|---|---|
| 5,755,715 A * | 5/1998 | Stern et al. ................ 606/31 |
| 5,906,614 A | 5/1999 | Stern et al. |
| 6,066,139 A | 5/2000 | Ryan et al. |
| 6,123,702 A | 9/2000 | Swanson et al. |
| 6,126,657 A | 10/2000 | Edwards et al. |
| 6,280,441 B1 | 8/2001 | Ryan |
| 6,451,015 B1 | 9/2002 | Rittman, III et al. |
| 2001/0014819 A1 | 8/2001 | Ingle et al. |

* cited by examiner

*Primary Examiner*—Rosiland Rollins
(74) *Attorney, Agent, or Firm*—Oliff & Berridge, PLC

(57) ABSTRACT

An electrosurgical method and apparatus comprises a probe, at least one temperature sensor, and a controller for generating and controlling electromagnetic energy supplied to the probe. The controller receives signals from the temperature sensor and controls the supply of electromagnetic energy such that the temperature of the probe is ramped up and then maintained at a steady state temperature of between 100° C. and 115° C. In an equilibration phase, between the ramping up and the steady state temperature, the controller holds the temperature of the probe substantially constant for a period of time to allow the temperature of different parts of the probe to equilibrate.

5 Claims, 3 Drawing Sheets

ELECTROSURGICAL METHOD AND APPARATUS

This nonprovisional application claims the benefit of U.S. Provisional Application No. 60/445,455, filed Feb. 7, 2003.

FIELD OF THE INVENTION

This invention relates to an electrosurgical system comprising an electrosurgical generator and a handpiece including electrosurgical electrodes. In particular, this invention is directed to electrosurgical systems capable of forming a lesion in body tissue, as is known for the treatment of various medical conditions including airway obstructions and sleep apnea.

BACKGROUND OF THE INVENTION

It is well known in the field of electrosurgery that there are two distinct tissue effects which can be achieved by RF, depending on the temperature to which the tissue is raised. The first is the removal of tissue by vaporisation, in which the electrode or electrodes are subjected to relatively high temperatures (typically over 1000° C.). The second is the production of tissue necrosis without the removal of tissue in situ, and it is to this second type of system to which the present invention is directed.

U.S. Pat. No. 5,843,021 discloses a typical example of this type of treatment, in which a probe including a tissue treatment electrode is placed in contact with body tissue, and an RF signal is supplied to the probe such that the electrode heats the tissue causing cell necrosis and forming a lesion. The lesion is subsequently absorbed by the body with the result that tissue shrinkage is seen to occur. This type of treatment has been successfully performed for a number of years, and is known as "Somnoplasty".

It is well known that to produce a lesion the temperature of the tissue should be kept below 100° C. Temperatures above 100° C. are known to cause charring and desiccation of the tissue (which can be undesirable as the desiccated tissue is unable to absorb any further RF energy). The prior art teaches that temperatures in the range of 80° C. to 100° C. are typical for this type of apparatus. Examples of prior art patents teaching temperatures in this range are U.S. Pat. No. 6,126,657, U.S. Pat. No. 4,411,266, U.S. Pat. No. 5,549,644, U.S. Pat. No. 5,456,682 and U.S. Pat. No. 6,056,745. As can be seen from these and any many other prior art documents, the instruction to maintain the temperature below 100° C. is well established. For example in U.S. Pat. No. 4,411,266 it is stated "any non-uniform hot spots must be monitored to prevent runaway flash heating to the boiling point of 100° C." U.S. Pat. No. 6,056,745 states "The maximum temperature condition T.sub.MAX lies within a range of temperatures which are high enough to provide deep and wide lesions (typically between about 90° C. and 98° C.), but which are safely below about 100° C., at which tissue desiccation or tissue boiling is known to occur." As can be seen, the direction to maintain the probe temperature below 100° C. is seen as an essential requirement for successful lesion generation.

The problem with this requirement to maintain the probe temperature below 100° C. is that this can lead to a relatively slow process, requiring anything up to several minutes of treatment time in order to generate the lesion. Unless the control of the energy delivered to the probe is exceptional, the safest way to ensure that the probe temperature does not under any circumstances exceed 100° C. is to drive the device such that its normal operating is well below 100° C. Many devices operate at temperatures of between 80° C. and 85° C. (see U.S. Pat. No. 4,411,266, for example), which can lead to even longer treatment times. The present invention seeks to provide a lesion generation system which can produce effective lesions using considerably reduced treatment times.

SUMMARY OF THE INVENTION

Accordingly, there is provided apparatus for forming a lesion in body tissue, the apparatus comprising;

i) a probe adapted to contact body tissue, and having at least one electrode, ii) at least one temperature sensor capable of measuring the temperature of the probe and generating signals representative of the temperature, and iii) a controller comprising generation means for generating electromagnetic energy and supplying the energy to the at least one electrode, and control means for receiving the signals from the at least one temperature sensor and controlling the generation means such that:

a) the temperature of the probe is ramped up to a first equilibration temperature, b) the temperature of the probe is held substantially constant at the equilibration temperature for a period of time to allow the temperature of different parts of the probe to equilibrate, and c) the temperature of the probe is then increased to and maintained at a final steady state temperature.

The control means is adapted to control the generation means such that there is an equilibration phase between the ramp-up phase and the steady state phase. In this equilibration phase, the temperature of the probe is held substantially constant for a period of time at an equilibration temperature to allow the temperature of different parts of the probe to equilibrate. The equilibration temperature is preferably between 90° C. and 105° C., and is typically substantially 100° C. This equilibration phase ensures that all parts of the probe are substantially at the same temperature, and eliminates "hot spots" which are actually at a higher temperature than that detected by the at least one temperature sensor. After the equilibration phase the temperature of the probe is raised to its final steady state operating temperature of between 100° C. and 115° C., preferably substantially 110° C. This equilibration process provides improved temperature control of the probe, and allows temperatures of between 100° C. and 115° C. to be used without the risk that some parts of the probe may be hot enough to cause charring of tissue.

The invention also resides in a method comprising the steps of providing a probe capable of contacting body tissue to be treated, delivering electromagnetic energy to the probe such as to raise the temperature of the tissue in contact with the probe, measuring the temperature of the probe, and controlling the delivery of the electromagnetic energy such that a) in an initial ramp-up phase, the temperature of the probe is raised rapidly to a first threshold temperature, b) in a second equilibrating phase, the temperature of the probe is held substantially constant for a period of time to allow the temperature of different parts of the probe to equilibrate, and c) in a subsequent treatment phase, the temperature of the probe is raised to a second, higher threshold temperature such that a lesion is formed in the tissue adjacent the probe without the complete removal of electrolytes in the tissue adjacent the probe though vaporisation.

As stated previously, the first threshold temperature is preferably between 90° C. and 105° C., and typically substantially 100° C. In one convenient arrangement the equilibrating phase takes place for a predetermined period of time, or alternatively takes place until a predetermined time from the start of the ramp-up phase. The second threshold temperature is conveniently between 100° C. and 115° C., preferably 105° C. and 115° C., and typically substantially 110° C.

The present invention is based on the surprising discovery that probe temperatures of slightly higher than 100° C. can produce effective lesions without producing the expected charring and desiccation of the tissue. As stated above, this is contrary to what has been a widespread prejudice against this practice in the field over many years. The explanation for this surprising discovery is not fully understood, but is believed to be based on the phenomenon that the heating of the tissue causes an increase in the concentration of the electrolyte in the tissue in the region of the probe. This causes the boiling point of the electrolyte to be increased, with the result that temperatures of up to 115° C. can be reached without causing charring or significant desiccation of the tissue. This increase in temperature has a considerable effect on treatment time, and it has been found that an acceptable lesion can be produced in around 60 seconds, as opposed to treatment times of 4 to 5 minutes with probes operated at only 85° C.

The invention will be further described, by way of example only, with reference to the accompanying drawings.

DETAILED DESCRIPTION OF THE PREFERRED EMBODIMENT OF THE INVENTION

Figure 1:
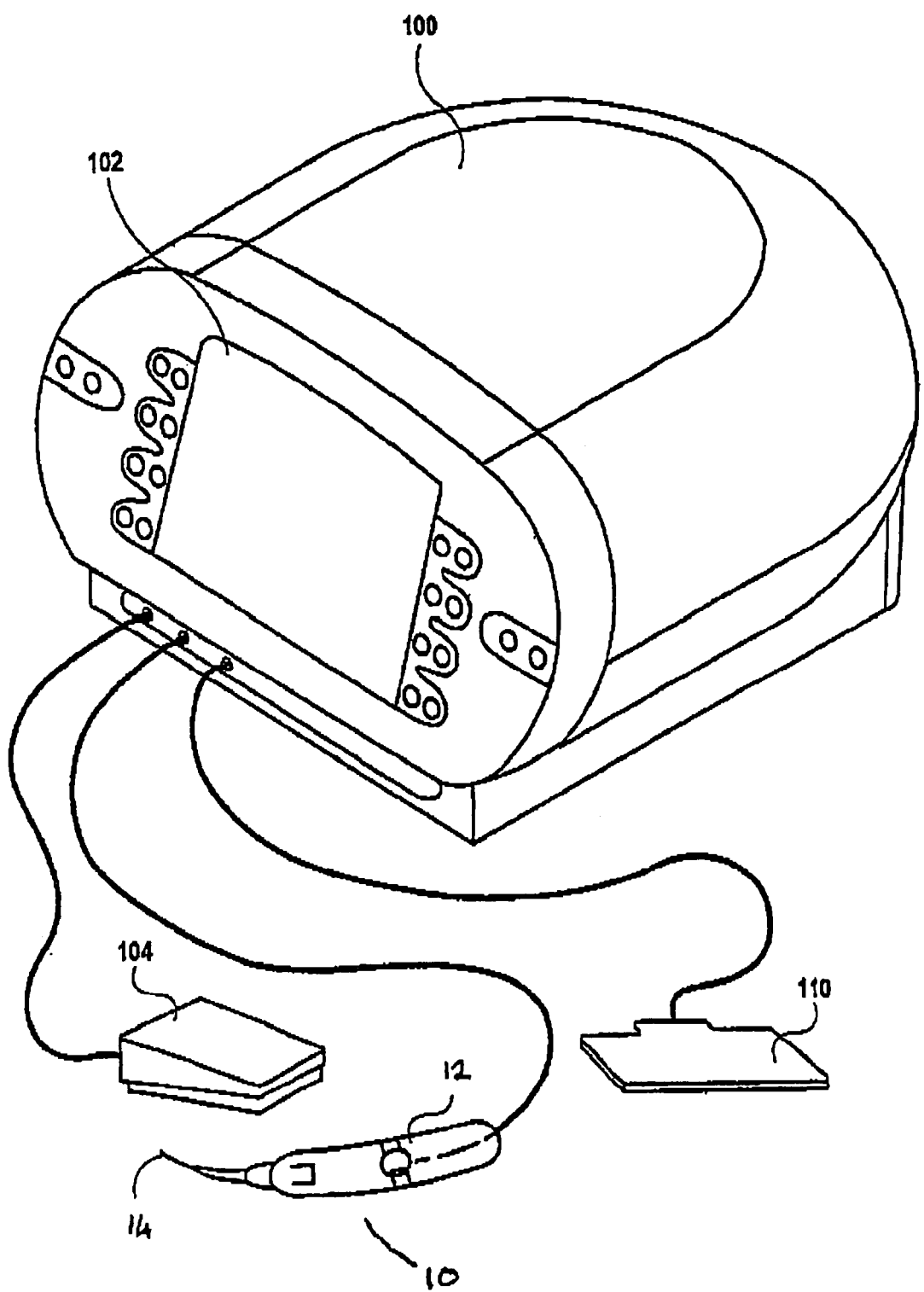
FIG. 1 is a schematic diagram of an electrosurgical system in accordance with the present invention.

FIG. 1 shows the apparatus for a typical embodiment of an RF electrosurgical device for forming lesions in body tissue. The system comprises a controller 100 (including an RF power supply) with a user input and display panel 102. Also provided are a foot switch 104, an electrical grounding pad 110 and a probe 10 including a surgical handpiece 12 with a surgical electrode 14. The user input allows the user to input different parameters to affect lesion size, including treatment duration, and total energy delivery.

The controller 100 converts the low frequency electrical energy supplied by a wall connection (not shown) into the high frequency or RF energy necessary for surgery. The user input and display panel 102 displays relevant parameters and provides buttons and switches for user input to the control systems. The foot switch 104 connected to the controller provides means for switching the unit on and off. The surgical handpiece 12 is also connected to the controller and is the means for delivering the RF energy to the surgical electrode 14. The electrical grounding pad 110 is also connected to the controller and floats at a reference electric potential. Other embodiments of this invention have no electrical grounding pad.

Figure 2:
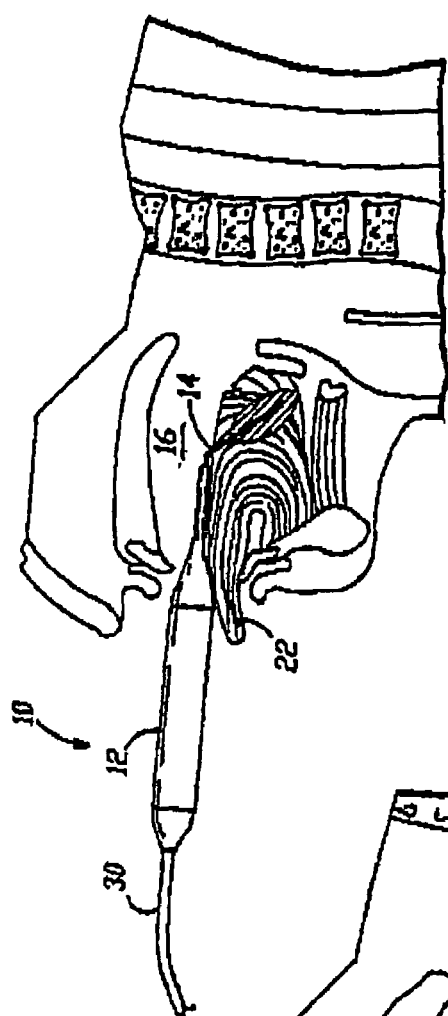
FIGS. 2 and 3 are schematic sectional views of the probe of FIG. 1, shown generating a lesion in the tongue of a patient.
Figure 3:
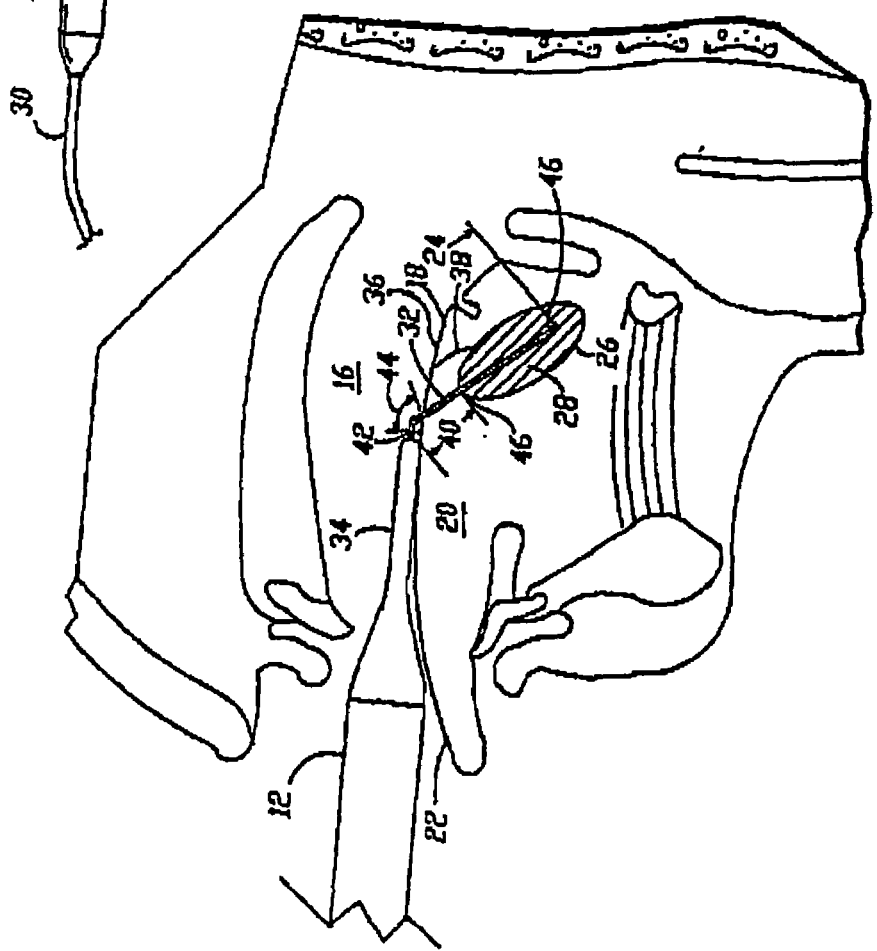

Referring now to FIGS. 2 and 3, the probe 10 is shown being used to reduce a volume of a selected site in an interior of a head and neck structure, and more particularly to a structure that is associated with an airway passage. Suitable anatomical structures include but are not limited to the tongue, uvula, soft palate tissue, tonsils, adenoids, turbinate structures and the like. In FIGS. 2 and 3, probe 10 is shown as including a handpiece 12 coupled to an electrode 14. Handpiece 12 can be a proximal portion of electrode 14 that is suitably configured to enable placement and removal of probe 10 to and from a selected anatomical structure and may include, in one embodiment, a proximal portion of electrode 14 that is insulated. Handpiece 12 and electrode 14 are sized and of a suitable geometry to be maneuverable in an oral cavity 16, pierce a tongue surface 18 and advance into an interior 20 of a tongue 22 a sufficient distance 24 to a tissue site 26. Electromagnetic energy is delivered to tissue site 26 to create cell necrosis at zone 28 without damaging a main branch of the hypoglossal nerve. A cable 30 is coupled to the electrode 14. For purposes of this disclosure, the main branches of the hypoglossal nerve are those branches which if damaged create an impairment, either partial or full, of speech or swallowing capabilities. Following the treatment, the treated structure of tongue 22 is repositioned in oral cavity 16. With this cell necrosis, the back of the tongue 22 moves in a forward direction away from the air passageway. The result is an increase in the cross-sectional diameter of the air passageway.

Handle 12 is preferably made of an electrically and thermally insulating material. Electrode 14 can be made of a conductive material such as stainless steel. Additionally, electrode 14 can be made of a shaped memory metal, such as nickel titanium, commercially available from Raychem Corporation, Menlo Park, Calif. In one embodiment, only a distal end of electrode 14 is made of the shaped memory metal in order to effect a desired deflection.

Probe 10 can include visualization capability including but not limited to a viewing scope, an expanded eyepiece, fiber optics, video imaging, and the like.

Electrode 14 can include an insulator 32 which can be adjustable in length and in a surrounding relationship to an exterior surface of electrode 14. Insulator 32 serves as a barrier to thermal or RF energy flow. Insulator 32 can be in the form of a sleeve that may be adjustably positioned at the exterior of electrode 14. In one embodiment the insulator can be made of a polyamide material and be a 0.002 inch (50 micron) shrink wrap. The polyamide insulating layer is semi-rigid.

Handpiece 12 can have a reduced diameter at a distal portion 34 to facilitate positioning, maneuverability, provide easier access to smaller openings and improve the visibility in the area where electrode 14 is to penetrate.

To use probe 10 in oral cavity 16, a topical and then a local anesthetic is applied to tongue 22. After a suitable period for the anesthesia to take effect, the physician may grasp the body of tongue 22 near the apex, using a gauze pad for a better grip. Tongue 22 is then drawn forward, bringing the body and the root of tongue 22 further forward for improved accessibility. Grasping handpiece 12, the physician positions a distal portion of electrode 14 at tongue surface 18. The position of electrode 14 in FIGS. 2 and 3, illustrates cell necrosis zone 28 below a mucosal surface 36 providing a protected zone 38. An insulated portion 40 of electrode 14 prevents delivery of energy to a main branch of a hypoglossal nerve and/or to mucosal surface 36.

Electrode 14 can have an angle 42 at a bend zone 44 which is lateral to a longitudinal axis of handpiece 12. Electrode 14 can be malleable to create different bend zones, depending on the anatomical structure and the insertion position of the anatomical structure. With the use of a bending fixture, not shown, the arc of angle 42 can be adjusted by the physician as needed at the time of treatment.

It will be appreciated that the term "electrode" in the specification generally means an energy delivery device. The device may be arranged to heat tissue using methods including but not limited to resistive heating and heating by RF, microwave, or ultrasound energy. The preferred energy source is an RF source and electrode 14 is an RF electrode operated in either bipolar or monopolar mode with a ground pad electrode. In a monopolar mode of delivering RF energy, a single electrode 14 is used in combination with an indifferent electrode patch that is applied to the body to form the other contact and complete an electrical circuit. Bipolar operation is possible when two or more electrodes 14 are used. Multiple electrodes 14 may be used.

When the energy source is RF, an RF energy source may have multiple channels, delivering separately modulated power to each electrode 14. This separate modulation reduces preferential heating that occurs when more energy is delivered to a zone of greater conductivity and less heating occurs around electrodes 14 which are placed into less conductive tissue. If the tissue hydration or blood infusion in the tissue is uniform, a single channel RF energy source may be used to provide power for the treatment and cell necrosis zones are relatively uniform in size.

One or more sensors 46 are included and positioned at a distal end of electrode 14, at a distal end of insulator 32, as well as at other positions on probe 10. Sensor 46 is of conventional design, including but not limited to thermistors, thermocouples, resistive wires, and the like. A suitable sensor 46 is a T type thermocouple with copper constantan, J type, E type, K type, fiber optics, resistive wires, thermocouple IR detectors, and the like.

Figure 4:
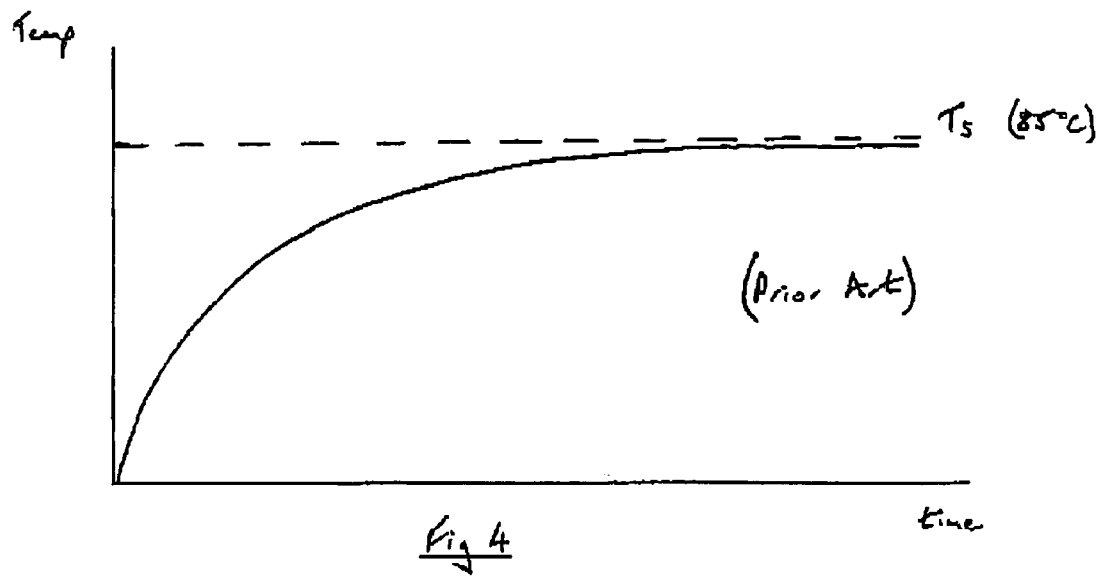
FIG. 4 is a graph of temperature against time, for a typical prior art lesion generation device.

FIG. 4 shows a schematic graph of the temperature profile of a typical prior art device. The sensors 46 feed back temperature readings to the controller 100 which compares the readings with a set point temperature $T_s$. This set point temperature may be 100° C., or depending on the nature of the control system, it may be less than 100° C., typically 85° C. The controller 100 compares the temperature detected by the sensors 46 with the set point temperature, and also takes into account the rate of change of the detected temperature since the previous reading. The controller 100 adjusts the RF power delivered to the electrode 14 in accordance with these calculations. Readings are taken and adjustments are made on a repeated basis, typically once per second. U.S. Pat. No. 5,057,105 describes one such temperature control technique in more detail.

Figure 5:
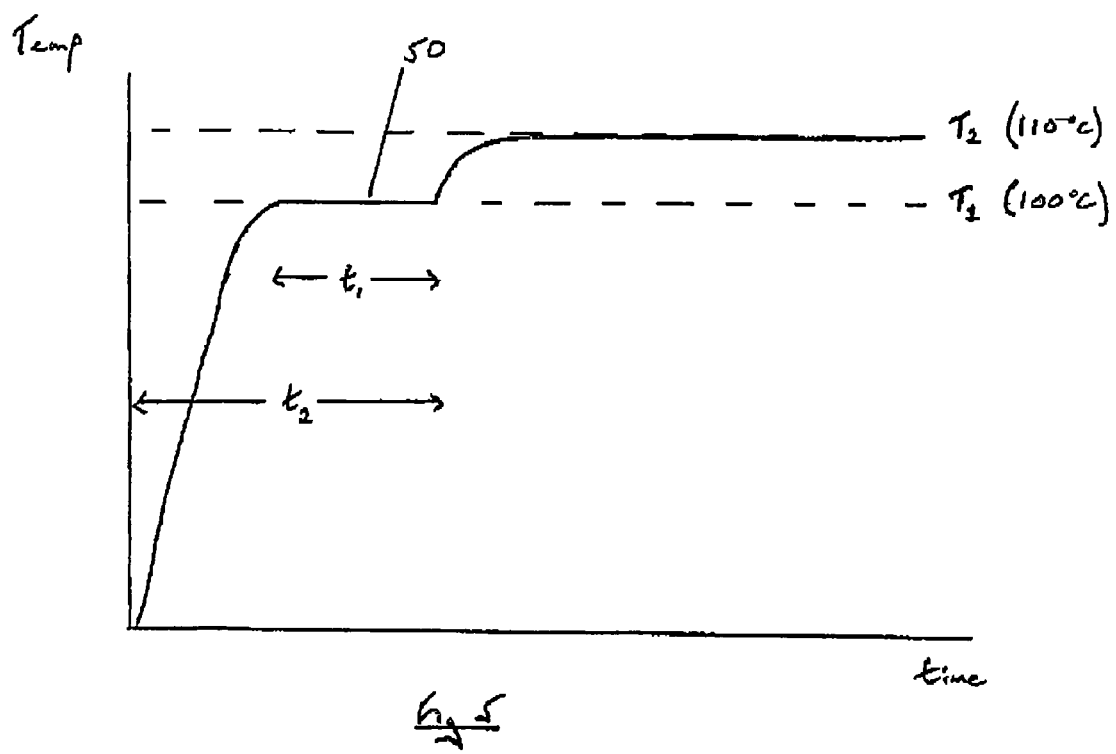
FIG. 5 is a graph of temperature against time, for a lesion generation device in accordance with the present invention.

FIG. 5 is a typical temperature profile in accordance with the apparatus and method of the present invention. The controller 100 supplies a relatively high power RF signal to the electrode 14 (typically around 10 W) such that the temperature of the probe 10 rises quickly. Temperature readings are taken every 60 ms. When the sensors 46 detect that the temperature of the probe 10 has reached a first threshold temperature $T_1$ (typically 100° C.), the controller reduces the power of the RF signal supplied to the electrode 14 to a relatively lower level (typically around 3 W). This is sufficient to hold the temperature of the probe at a constant temperature for a certain period of time, as shown at 50 in FIG. 5. This period of time is sufficient for the temperature of the probe to equilibrate, and become uniform over all parts of the probe 10. The equilibration period can be a predetermined period of time, as shown at $t_1$ in FIG. 5 (in which the equilibration period is a fixed period of e.g. 10 seconds). Alternatively, the equilibration period can subsist until a predetermined period of time has elapsed from the start of the process, as shown at $t_2$ in FIG. 5 (in which the equilibration period lasts until a period of e.g. 15 seconds from the start of the process).

Following the equilibration period, the higher power RF signal is resumed so that the temperature of the probe 10 continues to rise, until it reaches a second threshold temperature $T_2$ This second threshold temperature is above 100° C., and is typically 110° C. The controller 100 thereafter supplies sufficient power to the electrode 14 to maintain the probe substantially at the second threshold temperature for the remainder of the procedure, until the user proscribed treatment duration has elapsed, the required energy has been delivered, or until the footswitch is activated to switch off the RF signal and end the treatment process.

It has been found that the use of this higher treatment temperature, together with the added improvement in temperature control provided by the equilibration of the probe, has produced lesions comparable in size with those produced by the prior art devices, but with a greatly reduced treatment time and delivered energy. A typical prior art lesion generation device produces an acceptable lesion in around 4 to 5 minutes. The device of the present invention has been found to produce a lesion which is 70% of the size of the prior art lesion in only 60 seconds, and with only 40% of the delivered energy of the prior art system.

What is claimed is:

1. A method of forming a lesion in body tissue comprising the steps of providing a probe capable of contacting body tissue to be treated, delivering electromagnetic energy to the probe such as to raise the temperature of the tissue in contact with the probe, measuring the temperature of the probe, and controlling the delivery of the electromagnetic energy such that:
   a) in an initial ramp-up phase, the temperature of the probe is raised rapidly to a first threshold temperature of between 90° and 105° C.,
   b) in a second equilibrating phase, the temperature of the probe is held substantially constant for a period of time to allow the temperature of different parts of the probe to equilibrate, and
   c) in a subsequent treatment phase, the temperature of the probe is raised to a second, higher threshold temperature of between 100° C. and 115° C. such that a lesion is formed in the tissue adjacent the probe without the complete removal of electrolytes in the tissue adjacent to the probe through vaporisation.

2. A method of forming a lesion in body tissue according to claim 1, wherein the first threshold temperature is substantially 100° C.

3. A method of forming a lesion in body tissue according to claim 1, wherein the equilibrating phase takes place for a predetermined period of time.

4. A method of forming a lesion in body tissue according to claim 1, wherein the equilibrating phase takes place until a predetermined time from the start of the ramp-up phase.

5. A method of forming a lesion in body tissue according to claim 1, wherein the second threshold temperature is substantially 110° C.

* * * * *